United States Patent [19]
Pepe et al.

[11] 3,959,327
[45] May 25, 1976

[54] ORGANOFUNCTIONAL SILICON COMPOUNDS

[75] Inventors: Enrico J. Pepe; James G. Marsden, both of Amalwalk, N.Y.

[73] Assignee: Union Carbide Corporation, New York, N.Y.

[22] Filed: June 2, 1971

[21] Appl. No.: 149,324

[52] U.S. Cl. .................. 260/448.8 R; 260/46.5 R; 260/448.2 N
[51] Int. Cl. .............................................. C07f 7/18
[58] Field of Search ........................... 260/448.8 R

[56] References Cited
UNITED STATES PATENTS 3,404,168  10/1968  Simmler et al. .......... 260/448.8 R X
3,502,704   3/1970  McKellar ................... 260/448.8 R Primary Examiner—Daniel E. Wyman
Assistant Examiner—P. F. Shaver
Attorney, Agent, or Firm—George A. Skoler

[57] ABSTRACT

The invention relates to novel silicon compounds formed by the reaction of a thiolactone or polythiolactone and an aminoalkyl silane or siloxane. These materials are useful to enhance adhesion of various resins and elastomers to inorganic substrates or to accellerate the cure of elastomers.

5 Claims, No Drawings

ORGANOFUNCTIONAL SILICON COMPOUNDS

This invention relates to a new silicon-containing composition of matter, more particularly a silicon-containing composition of matter which contains an amide group and is the reaction product of a thiolactone or a polythiolactone with an aminoorgano silicon compound.

This invention is directed to silicon compounds having the average formula:

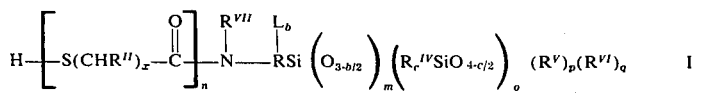

wherein $x$ is about 2 to about 8; $n$ is at least 1 and can be as large as 1000 or more; $b$ is 0, 1, 2 or 3; $c$ is one or more of 0, 1, 2 and 3; $m$ is 0 or 1; $o$ is 0 or a positive number and when $o$ is a positive number, $m$ is 1; $p$ is equal to 3-b when $m$ is 0 and $o$ is 0, and when $m$ is 1, $p$ is 0; $q$ is 0 when $p$ is equal to 3-$b$ and $q$ is 0 or a positive number when $m$ is 1;

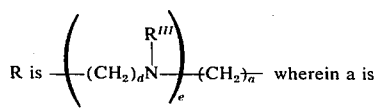

at least 3, typically not greater than 12, $d$ is at least 2 and typically not greater than 8, and $e$ is 0 or a positive number, preferably 0, 1 or 2; each $R^{II}$ is hydrogen and/or alkyl of 1 to about 4 carbon atoms; each $R^{III}$ is one of hydrogen, alkyl, cycloalkyl, aryl, acyl, aminoalkyl, hydroxyalkyl, which alkyls contain 1 to about 8 carbon atoms, and H-S(CHR″)$_x$

L is alkyl of 1 to about 6 carbon atoms; $R^{VII}$ is hydrogen, alkyl of 1 to about 4 carbon atoms or phenyl; $R^{IV}$ is silicon bonded and is a hydrolyzable and condensable group such as hydroxyl, halide, alkali metaloxy, alkoxy, aroxy, acyloxy and the like; and $R^{VI}$ is bonded to oxygen and is hydrogen, alkyl, alkali metal, aryl, acyl and the like.

The silicon compound of Formula I are obtained by the reaction of a thiolactone or a polythiolactone with a silicon compound having the average formula:

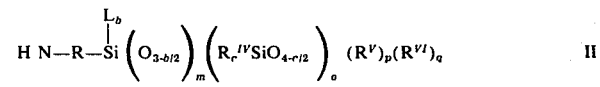

Illustrative of $R^{III}$ and L (each limited by the description above), in the formula I above, are organic radicals such as alkyl, cycloalkyl, aryl, acyl, and the like, such as alkyl of 1-8 carbon (for example, methyl, ethyl, propyl, n-hexyl, and the like), aryl (such as phenyl, naphthyl, anthracyl, and the like); cycloaliphatic (such as cyclohexyl, cyclooctyl and the like); acyl (such as formyl, acetyl, propionyl, butyryl, stearyl and the like) or the corresponding acid to form an amino salt and the term "acyl" includes such salts; aminoalkyl (such as aminomethyl, gamma-aminopropyl, delta-aminobutyl, and the like); hydroxyalkyl (such as hydroxymethyl, gamma-hydroxypropyl) and the like.

$R^{IV}$ is an organic radical bonded to silicon by a carbon to silicon bond when it is other than hydrogen. Illustrative radicals include those cited for $R^{III}$ above, as well as other organic radicals such as urea substituted hydrocarbons, and essentially any other organic radical which does not significantly interfere with the reaction product of this lactone or polythiolactone and the amino substituted silicon compound of Formula II to the formed compound characterized by Formula I.

With respect to the substituents present in the silicon compounds encompassed by Formula II, none should interfere with the reaction of the thiolactone or the polythiolactone with the amino substituent to form the compounds of Formula I. This represents the only real limitation in the nature of the amino substituted silicon compounds encompassed by Formula II. It is true that certain substituents as hydroxyalkyl might interfere or compete in the reaction with thiolactone or polythiolactone, but the statistical result of such competitive reactions will result in an insolatable product which is encompassed for Formula I.

The amines which may be treated in accordance with the process of this invention are those which are described in U.S. Pat. No. 2,971,864, patented Feb. 14, 1961, specific embodiments being illustrated in Examples 1, 2, 3, 4 and 6 thereof; U.S. Pat. No. 2,832,754, particularly at Examples 1, 2, 3 and 4 thereof; and U.S. Pat. NO. 2,942,019 at columns 1, 2, 3 to line 17 of column 4 with respect to silanes and siloxane homopolymers and copolymers which are described therein to be reacted with aldehydes and ketones.

The thiolactones reacted with the silicon compound of Formula II to produce the product of Formula I are encompassed by the formula:

wherein each $R^{II}$ and $x$ are defined above. Illustrative of lactones covered by Formula III are betapropiothiolactone; 2-butyrothiolactone; 2-valerothiolactone; epsilon-thiocaprolactone, alkyl substituted epsilon-thiocaprolactone, and the like. Illustrative of the substituted thiolactones are the various monoalkyl epsilon-thiocaprolactones, such as the monomethyl, monethyl, monopropyl, monoisopropyl-, and the like, dialkyl epsilon-thiocaprolactones in which the two alkyl groups are substituted on the same or different carbon atoms but not both on the epsilon carbon atom; trialkyl epsilon-thiocaprolactones in which two or three carbon atoms in the lactone ring are substituted, so long as the epsilon carbon atom is not di-substituted.

The polythiolactones reacted with the silicon compound to produce the product of Formula I are those encompassed by the formula:

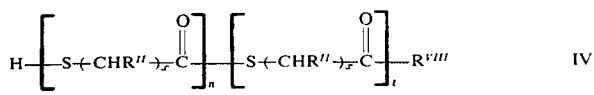

wherein $R^{VIII}$ is the residue of the polymerization initiator, and $t$ is 0 or a positive number. Suitable procedures for making polythiolactones are described by C. G. Overberger and F. Weise, *J. Polymer Science*, B2, 239(1964); J.A.C.S., 90, 3533(1968). In general, the polymers are formed by the initiation of the ring opening of the thiolactone in the presence of an active hydrogen compound and an alkali metal, alkaline earth metal or transition metal catalyst, or the corresponding salts of these metals and the active hydrogen compound.

The process to produce the silicon compounds of Formula I involves reacting the appropriate silicon compound of Formula II with the desired thiolactone of Formula III or polythiolactone of Formula IV. In the case of the reaction with the thiolactone of Formula III, it can occur at extremely low temperatures to higher temperatures depending upon the nature of the reactants. In the case of thiolactones having 5 ring carbon atoms or less, the reaction is favorably conducted in the presence of a solvent at moderate temperatures, viz., 100°C. and below. The reaction in the case of thiolactones containing more than 5 carbon atoms specifically 6 carbon atoms and greater, temperatures higher than 100°C. are normally employed since the reaction is not quite as fast and heat input is generally needed. Because the reaction of the thiolactone with the amino group of the silicon compound of Formula II is essentially quantitative in respect to the amino, the products can be isolated simply by removal of solvent employed or any excess thiolactone, preferably under reduced pressure. In the case of the reaction of the thiolactones containing less than 5 carbon atoms, it is desirable because of the apparent exothermic nature of the reaction to control the rate of reaction with solvent. The solvent acts as a heat transfer agent to help dissipate the heat generated by the reaction and to assist the course of the reaction to give the desired product. Illustrative solvents include, by way of example, chloroform, 1,1,2-trichloroethylene, sym.-tetrachloroethylene, monochlorobenzene, dimethyl ether, diethyl ether, di-n-propyl ether, diisopropyl ether, tetrahydrofuran, dimethyl ether of ethylene glycol and the like; nitriles such as acetonitrile, propionitrile, butyronitrile, and the like; tertiary amides such as N,N-dimethyl formamide and N,N-dimethyl acetamide and the like; dialkyl sulfoxides such as dimethyl sulfoxide, diethyl sulfoxide, and the like.

In the case of the lower thiolactones, that is, 5 carbon atoms or less, the solvent, when used, is typically employed in an amount equal in volume to the amount of amine used, that is, an equal volume amount of solvent to the volume of the silicon compound of Formula II employed. However, this volume ratio can vary from about 0.01 to about 10 volumes of solvent for each volume of the aminosilicon compound of Formula II without undue effect on the course of reaction. Volume ratios of solvent to silicon compound of Formula II of about 0.5 to about 2 are preferred.

In the case of these lower thiolactones, it is oftentimes important to exert care in the manner of combining the reactants. The preferred method involves adding the lower thiolactone to a solvent solution of the aminosilicon compound of Formula II. In this way, one can easily control the temperature of the reaction.

In the case of the lower thiolactones the reaction of silicon compound of Formula II with the thiolactone is typically exothermic, and therefore, to minimize the effect of heat of reaction, it is desirable to employ relatively low temperatures, viz., below about 40°C., typically in the range of about 0°C. to about 10°C. If the amino group is primary, then the reaction generally moves with great rapidity in the case of these lower thiolactones, but when the amine is secondary, the reaction is generally more sluggish, and therefore, it may be desirable in such cases to introduce heat to the reaction, typically to temperatures not in excess of the boiling point of the aminosilicon compound characterized by Formula II. When reacting the lower thiolactones, it is desirable not to run the reaction at temperatures greater than the boiling point of the solvent employed. However, in the case of the higher thiolactones, the reaction between the thiolactone and the aminosilicon compound of Formula II may be considerably higher, typically greater than about 100°C. and may range as high as 300°C. Generally, these higher thiolactones favorably react at temperatures in the range of about 150°C. to about 240°C.

In the case of these higher thiolactones, it is oftentimes desirable to employ a catalyst to induce the reaction. Useful catalysts for these purposes are alkali metal, alkaline earth metal and tin catalysts, such as described in U.S. Pat. No. 2,890,208, patented June 9, 1959, other metal catalysts such as described at column 9 of U.S. Pat. No. 3,169,945, patented Feb. 16, 1965, the acid catalysts described at column 1, lines 37–40 of U.S. Pat. No. 2,914,556, patented Nov. 24, 1959, and the process described in U.S. Pat. No. 3,284,417.

The reaction of the thiolactone with the aminosilicon compound of Formula II may be effected with heat alone, though the higher molecular weight products containing polythioester are more difficult to obtain by this procedure.

In most cases, the reaction of the thiolactone with the aminosilicon compound of Formula II is quantitative; consequently, equal mole amounts of the reactants can be employed to give complete conversion of the amino groups to hydroxy alkylamide or polyester amide. However, to insure complete reaction, it is generally preferred to carry out the reaction using an excess of thiolactone or a mole amount at least comparable to the value of $n$ defined in Formula I. Thus the ratio of thiolactone to the silicon compound of Formula II is dependent upon the desired molecular weight indicated by the value of $n$. If $n$ is to be 1, then an equal mole ratio or slight excess of thiolactone to aminosilicon compound may be employed, such as mole ratios of 1:1 to 3:1 with preferred ranges being 1:1 to 1.1:1. In the case of higher molecular weight polythiolactones (i.e., polythioesters) characterized by Formula I, the molecular ratio of thiolactone to aminosilicon compound of Formula II can be as high as 1000:1, preferably not greater than about 100:1.

The reaction between the polythiolactone of Formula IV and the aminosilicon compound of Formula II is achieved by the transamidation of the aminosilicon compound into the chain of the polythiolactone. The site of attack by the amino group is at a $$-\overset{\text{C}}{\underset{\|}{\text{C}}}-\text{S}-$$

unit of the polymer causing it to break at the carbonoxy $$(-\overset{\text{O}}{\underset{\|}{\text{C}}}-)-$$

sulfur bond forming an amide $$(-\overset{\text{O}}{\underset{\|}{\text{C}}}-\text{NH}-)$$

and a mercapto group (HS—) which terminates the unjoined portion of the polythiolactone. The degree of transamidation obtainable is dependent upon the number ratio of the amino groups of the silicon compound and the thiocarbonyl $$(-\overset{\text{O}}{\underset{\|}{\text{C}}}-\text{S}-)$$

groups in the polythiolactone. The higher the ratio, up to 1, the greater the degree of transamidation and the lower the value of $n$ will result. In the case of maximum transamidation, $n$ will have a value of about 1. In such a case, any such $n$ values within the value of $t$ will be cleaved from the polythiolactone to form the product of Formula I. At the other extreme, when the aforementioned ratio approaches zero, then $n$ has the potential of being a maximum value, but is, however, dependent upon the arbitrariness of the transmidation reaction. Whenever the value of the sum of $n$ and $t$ of Formula IV far exceeds the value of $n$, such as at least two times the maximum value of $n$, then there is an excellent opportunity to produce a product of Formula I wherein $n$ possesses the maximum or is in the range of the maximum value of $n$.

Such transamidation is simply achieved by mixing an amount of polythiolactone and aminosilicon compound of Formula II in the desired number ratio of amino to thiocarbonyl and heating the mixture to a temperature at which there is noted a reduction in the viscosity of the mixture and the reaction is continued until the viscosity becomes constant, i.e., it ceases to drop. Such a reaction can be effected at room temperature (about 25°C.), where the reaction is slow, to higher temperatures, i.e., greater than 75°C., where the reaction is more rapid. Temperatures greater than 300°C. are not regarded to provide any advantage and from a practical standpoint, such can be considered to be the upper limit of the reaction.

The transamidation reaction is desirably carried out neat, i.e., in the absence of a solvent, at a temperature at which the mixture is liquid. If the polythiolactone is normally solid, then the mixture can be formed above its melting point. If a solvent is desired, one of those previously mentioned may be employed.

The silicon compounds of this invention have a number of utilities. The high molecular weight polythiolactone silicon polymers where $n$ is 10, or greater, are readily compatible in a number of resins such as polyurethane resins, polyvinylchloride resins, phenolic resins, and butadiene-styrene or butadieneacrylonitrile and can be used as plasticizers or cure accellerators therefor. If the silicon compound of Formula I is either hydrolyzable or condensable, then such product also improves the bond of the resins to a plurality of substrates such as glass (glass fiber and plate glass), metal, metal oxide fillers (including siliceous fillers) and the like.

Though the examples below demonstrate specific embodiments of this invention, it is not intended that the invention be limited thereby.

EXAMPLE 1

Into a 100 ml. 3-necked flask equipped with magnetic stirrer, thermometer, heating mantle and protected from the atmosphere by a dry nitrogen gas by-pass at the exit port are charged 22.1 gms., 0.1 moles, of $NH_2(CH_2)_3Si(OC_2H_5)_3$ and 14.3 gms., 0.11 moles, of epsilon-thiocaprolactone, $$\left[-\overset{\text{O}}{\underset{\|}{\text{SC}}}(CH_2)_5-\right].$$

The stirred mixture is heated to 125°C. for 6 hours. Titration of residual amine at the end of this period, using brom cresol green indicator in isopropanol and 0.1 N HCl, indicates the reaction is 99.8 mole % complete. Vacuum distillation of all low boiling materials to 125°C. at 1mm. of mercury pressure produces 32.2 gms. of adduct in 91.7 weight % yield. Continued distillation of the latter residue isolates 27.2 gms., .0775 moles, of high purity $$HS(CH_2)_5\overset{\text{O}}{\underset{\|}{\text{C}}}\overset{\text{H}}{\text{N}}(CH_2)_3Si(OC_2H_5)_3$$

in 77.5 mole % conversion; B.P.- 202±2°C/0.5 mm of mercury pressure, $n_0^{25}$ 1.4695.

EXAMPLE II

Into a 100 ml 3-necked flask outfitted with mechanical stirrer, thermometer, heating mantle and dry nitrogen by-pass of the exit port are charged 28.1 gms., 0.106 moles, of $NH_2CH_2CH_2NHCH_2CH_2NHCH_2CH_2CH_2\ Si(OCH_3)_3$ containing 0.318 moles of amino group, 32.5 gms., 0.25 moles of $$\left[-\overset{\text{O}}{\underset{\|}{\text{SC}}}(CH_2)_5-\right]$$

and 0.12 gms., 0.2 wgt%, of manganous benzoate. The stirred mixture is heated to 100°C. for 2 hours at which point an additional 9.1 gms., 0.07 moles, of epsilon-thiocaprolactone are added. Heating at 100°C. for 1 hour is followed by heating at 120°C. for 2 hours, at 135°C. for 1 hour and at 180°C. for 18 hours. At this point titration of residual amine as described in the previous example shows the conversion is 90 mole % complete to the product $$HS(CH_2)_5\overset{\text{O}}{\underset{\|}{\text{C}}}\overset{\text{H}}{\text{N}}\ CH_2CH_2\overset{}{\text{N}}CH_2CH_2\ \underset{\underset{(CH_2)_5SH}{\overset{\|}{C=O}}}{\overset{\overset{\text{O}}{\|}}{\underset{|}{C(CH_2)_5SH}}}N(CH_2)_3\ Si(OCH_3)_3.$$

EXAMPLE III

A mixture of 130 grams, 1.0 mole, of polyepsilon-thiolactone and 66.3 grams, 0.1 mole, of Δ-HN$_2$(CH$_2$)$_4$SiMe$_2$O(Me$_2$SiO)$_5$SiMe$_2$(CH$_2$)$_4$NH$_2$ is charged to a 550 ml. resin kettle outfitted with mechanical stirrer, thermometer and vacuum take-off and heated to 150°C. for 18 hours. Vacuum stripping to 150°C. at a pressure of 0.1 mm. of mercury pressure gives no appreciable loss in weight as volatile by-product. The resulting homogeneous viscous product copolymer is characterized by the formula:

where $n$ ranges from 1 to about 20 and has an average value of 5.

EXAMPLE IV

A mixture of 130 grams, 1.0 mole, of polyepsilon-thiocaprolactone and 102 grams, 0.1 mole, of

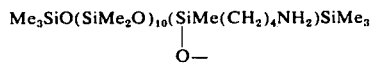

is reacted in the same manner as described in the previous example, except at 175°C. for 16 hours to produce a homogeneous formula: product copolymer that is characterized by the formula:

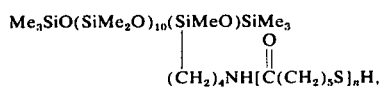

where $n$ ranges from 1 to about 20 and has an average value of 10.

EXAMPLE V

A mixture of 130 grams, 1.0 mole of high purity epsilon-thio-caprolactone, 2.21 grams, 0.01 mole, of NH$_2$(CH$_2$)$_3$Si(OEt)$_3$, 0.5 mole-% of stannous octoate, based upon the moles of reactants, and 132 grams of cumene solvent are heated to 100°C for 2 hours in a steam bath. On stripping the reaction mixture to 100°C. under vacuum there is obtainable the product characterized by the formula:

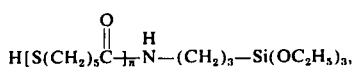

where $n$ ranges from 1 to about 1,000 and has an average of about 100.

"Me" in the examples means methyl, "Et" means ethyl, and "C$_2$H$_5$" is ethyl.

What is claimed is:

1. The silicon compounds having the average formula:

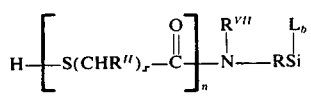

wherein $x$ is about 2 to about 8; $n$ is at least 1; $b$ is 0, 1, 2 or 3; $c$ is one or more of 0, 1, 2 and 3; $p$ is equal to 3-$b$,

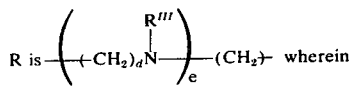

(CH$_2$)$_a$ is bonded to Si; $a$ is at least 3; $d$ is at least 2; and $e$ is 0 or a positive number; each $R^{II}$ is hydrogen or alkyl of 1 to about 4 carbon atoms; each $R^{III}$ is one of hydrogen, alkyl, cycloalkyl, aryl, acyl, aminoalkyl, hydroxyalkyl, which alkyls contain 1 to about 8 carbon atoms, and

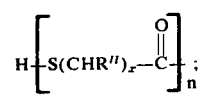

L is alkyl of 1 to about 6 carbon atoms; $R^{VII}$ is hydrogen, alkyl of 1 to about 4 carbon atoms or phenyl; $R^V$ is silicon bonded and is a hydrolyzable or condensable group.

2. The process of manufacturing the silicon compounds of claim 1 which comprises reacting a thiolactone with an aminosilicon compound having the average formula:

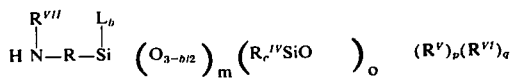

wherein R, $R^{VII}$, $R^{IV}$, $R^V$, $R^{VI}$, L, b, c, m, o, p and q have the definitions recited for each as set forth in claim 1.

3. The process of claim 2 wherein the thiolactone has the formula:

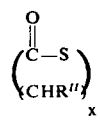

wherein $R^{II}$ is hydrogen or alkyl of 1 to about 4 carbon atoms and x is about 2 to about 8.

4. The process of manufacturing the silicon compounds of claim 1 which comprises transamidating a polythiolactone with an aminosilicon compound of the formula

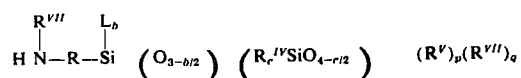

wherein R, $R^{VII}$, $R^{IV}$, $R^V$, $R^{VI}$, L, $b$, $c$, $m$, $0$, $p$, and $q$ are defined as in claim 1.

5.

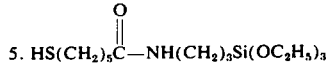

* * * * *

UNITED STATES PATENT OFFICE
CERTIFICATE OF CORRECTION

Patent No. 3,959,327  Dated May 25, 1976

Inventor(s) E. J. Pepe, et al.

It is certified that error appears in the above-identified patent and that said Letters Patent are hereby corrected as shown below:

Column 1, lines 36-39, "$H-S(CHR^{II})_x$ $$-\overset{O}{\underset{||}{C}}_{\overline{n}}$$

should read $$-- \quad H-S(CHR^{II})_x-\overset{O}{\underset{||}{C}}_{\overline{n}} \quad --$$

Column 2, line 29, "for" should read -- by --.

Column 3, line 61, "0.01" should read -- .1 --.

Column 7, line 3, first part of formula, "$HN_2$" should read -- $NH_2$ --.

Column 7, line 31, "formula" should read -- viscous --.

Column 8, line 34, the middle of the formula, "$(R_c^{IV}SiO)_o$" should read -- $(R_c^{IV}SiO_{\frac{4-c}{2}})_o$ --

UNITED STATES PATENT OFFICE
CERTIFICATE OF CORRECTION

Patent No. 3,959,327     Dated  May 25, 1976

Inventor(s) E. J. Pepe, et al.

It is certified that error appears in the above-identified patent and that said Letters Patent are hereby corrected as shown below:

Column 8, line 61, "O" should read -- o --.

Signed and Sealed this

Sixth Day of September 1977

[SEAL]

Attest:

RUTH C. MASON  
*Attesting Officer*

LUTRELLE F. PARKER  
*Acting Commissioner of Patents and Trademarks*